United States Patent
Montegrande (10) Patent No.: US 6,544,185 B2
(45) Date of Patent: Apr. 8, 2003

(54) ULTRASOUND IMAGING MARKER AND METHOD OF USE

(76) Inventor: Valentino Montegrande, 1150 Main St., Irvine, CA (US) 92614

( * ) Notice: Subject to any disclaimer, the term of this patent is extended or adjusted under 35 U.S.C. 154(b) by 0 days.

(21) Appl. No.: 10/033,535

(22) Filed: Oct. 23, 2001

(65) Prior Publication Data

US 2002/0151797 A1 Oct. 17, 2002

Related U.S. Application Data

(60) Provisional application No. 60/242,068, filed on Oct. 23, 2000.

(51) Int. Cl.[7] ................................................. A61B 8/00
(52) U.S. Cl. ..................................................... 600/458
(58) Field of Search ................................ 600/437, 443, 600/447, 458

(56) References Cited

U.S. PATENT DOCUMENTS

| | | |
|---|---|---|
| 3,818,894 A | 6/1974 | Wichterle et al. |
| 4,007,737 A | 2/1977 | Kvavle et al. |
| 4,041,931 A | 8/1977 | Elliot et al. |
| 4,202,349 A | 5/1980 | Jones |
| 4,331,654 A | 5/1982 | Morris |
| 4,693,237 A | 9/1987 | Hoffman et al. |
| 4,909,250 A | 3/1990 | Smith |
| 5,236,410 A | 8/1993 | Granov et al. |
| 5,281,408 A | 1/1994 | Unger |
| 5,334,381 A | 8/1994 | Unger |
| 5,421,336 A * | 6/1995 | De Bernardis ............... 600/461 |
| 5,422,730 A | 6/1995 | Barlow et al. |
| 5,494,030 A | 2/1996 | Swartz et al. |
| 5,636,255 A | 6/1997 | Ellis |
| 5,664,582 A | 9/1997 | Szymaitis |
| 5,676,146 A | 10/1997 | Scarborough |
| 5,676,925 A | 10/1997 | Klaveness et al. |
| 5,688,490 A | 11/1997 | Tournier et al. |
| 5,840,030 A * | 11/1998 | Ferek-Petric et al. ....... 600/439 |
| 5,853,366 A | 12/1998 | Dowlatshahi |
| 5,902,310 A | 5/1999 | Foerster et al. |
| 5,941,890 A | 8/1999 | Voegele et al. |
| 6,026,818 A | 2/2000 | Blair et al. |
| 6,161,034 A | 12/2000 | Burbank et al. |
| 6,173,715 B1 | 1/2001 | Sinanan et al. |
| 6,181,960 B1 | 1/2001 | Jensen et al. |
| 6,228,055 B1 | 5/2001 | Foerster et al. |
| 6,270,464 B1 | 8/2001 | Fulton, III et al. |

FOREIGN PATENT DOCUMENTS

| | | | |
|---|---|---|---|
| EP | 0 481 685 A1 | 4/1992 | |
| EP | 0 679 372 A2 | 2/1995 | |
| EP | WO 9608208 A1 | 3/1996 | |
| EP | WO 98/06346 | 2/1998 | |
| WO | WO 98/08440 | * 3/1998 | ............ A61B/8/08 |

* cited by examiner

*Primary Examiner*—Francis J. Jaworski
(74) *Attorney, Agent, or Firm*—Eric Karich (57) ABSTRACT

An ultrasound imaging marker has a marker body that is constructed of an ultrasound resonant material and that includes a resonant pocket. The marker body includes an interior surface and preferably an angled surface. The resonant pocket provides a feature that is easily visible to the ultrasound device. The interior surface is preferably coated with a metallic resonant layer such as alumina or gold. The angled surface bounds the interior surface and connects the interior surface with the perimeter lip. The ultrasound imaging marker is preferably used in conjunction with an insertion device for inserting the ultrasound imaging marker adjacent the location.

26 Claims, 8 Drawing Sheets

ULTRASOUND IMAGING MARKER AND METHOD OF USE

CROSS-REFERENCE TO RELATED APPLICATIONS

This application for a utility patent claims the benefit of U.S. Provisional Application No. 60/242,068, filed Oct. 23, 2000.

STATEMENT REGARDING FEDERALLY SPONSORED RESEARCH

Not Applicable

BACKGROUND OF THE INVENTION

1. Field of the Invention

This invention relates generally to markers used for marking a location in a mammalian body, and more particularly to an ultrasound imaging marker that allows a surgeon to locate a location in a mammalian body using an ultrasound imaging apparatus.

2. Description of Related Art

The following art defines the present state of this field:

The first class of markers include materials that have different ultrasound reflective properties and only remain in the body temporarily, eventually being reabsorbed by the body. An example of this technology is shown in Burbank et al., U.S. Pat. No. 6,161,034 (SENOREX®), that teaches detectable markers that may be introduced by a cavity created by removal of a biopsy specimen to mark the location of the biopsy site so that it may be located in a subsequent medical/surgical procedure. The marker preferably includes gasses, saline solutions, or similar materials. The markers remain present in sufficient quantity to permit detection and location of the biopsy site at the first time-point (e.g., 2 weeks) after introduction but clear from the biopsy site or otherwise not interfere with imaging of tissues adjacent the biopsy site at a second time-point several months after introduction.

Fulton, III et al., U.S. Pat. No. 6,270,464, teaches a biopsy localization device constructed of a bioabsorbable such as dehydrated collagen that is delivered in a pre-delivery state and swells within the body to a post-delivery state in which the device is palpably harder then the surrounding tissue.

Foerster et al., U.S. Pat. No. 6,228,055, teaches an implantable marker device for marking the location of a biopsy. The marker device can be constructed of a biodegradable polymer or other plastic, as long as they are constructed of a material that is biocompatible, implantable, and visible using an imaging system. The marker is preferably delivered using a stereotactic guidance system.

Voegele et al., U.S. Pat. No. 5,941,890, teaches an implantable marker having a base, an elevated bridge, and a pair of legs that are useful for fixing the marker in the tissue that is to be marked. The marker preferably includes camming marker surfaces that motivate the marker from the closed to open configurations. The marker can be constructed of either a metallic material, or an absorbable polymer.

Unger, U.S. Pat. No. 5,281,408, teaches a substantially homogeneous aqueous suspensions of low density microspheres which are presented as contrast media for imaging the gastrointestinal tract and other body cavities using computed tomography. In one embodiment, the low density microspheres are gas-filled. With computed tomography, the contrast media serve to change the relative density of certain areas within the gastrointestinal tract and other body cavities, and improve the overall diagnostic efficacy of this imaging method.

Unger, U.S. Pat. No. 5,334,381, teaches liposomes suitable as ultrasound contrast agents which contain media of various types including gases, gaseous precursors activated by pH, temperature or pressure, as well as other solid or liquid contrast enhancing agents. Methods of using the same as ultrasound contrast agents are also disclosed. The present invention also comprises novel methods for synthesizing liposomes having encapsulated therein gases.

Klaveness et al., U.S. Pat. No. 5,676,925, teaches a gas containing, or gas generating, polymer microparticles or microballoons used as a contrast agent in ultrasound imaging.

Scarborough, U.S. Pat. No. 5,676,146, teaches a surgical implant containing a resorbable radiopaque marker that enables the position and/or orientation of the implant to be readily determined by x-ray or other radiographic technique following its surgical implantation into the body.

Smith, U.S. Pat. No. 4,909,250, teaches an animal identification system for swine or other livestock which employs an identification implant or pellet consisting of food grade material and imprinted with information to identify the source of the animal and its carcass after slaughter. The pellet is implanted under the hide or skin of the animal for purposes of identification. In the case of swine, the identification pellet is located in the fat layer of the shoulder area underneath its hide or skin. The pellet and the imprinted information consist of food grade material which is capable of being dissolved with the fat layer or disintegrated into cracklings in a rendering process. The pellet remains in the carcass after the animal is slaughtered until its removal to permit identification of the source of the animal. If the pellet is not removed, it is either dissolved with the fat of the animal or disintegrated into cracklings in the rendering process. Installation tools are disclosed for implanting the identification pellet in a horizontal or vertical orientation under the hide or skin of the animal.

Many references utilize metal reference markers that are then observed using x-rays. Example of these devices are as follows:

Kvavle et al., U.S. Pat. No. 4,007,732, describes X-ray techniques that are used to detect early evidence of breast cancer. When such evidence is found, a target is implanted in the suspect area while the patient is being x-rayed. The target has an attached line which leads from the target out through the skin of the patient. A biopsy is made with a cutting tool guided on the line attached to the target, thereby obtaining a biopsy specimen accurately centered on the suspect area.

Liprie, U.S. Pat. No. 5,282,781, teaches a composite source wire for use in treating malignant tumors within a patient's body by localized in vivo radiation with a radioactive source, via a catheter providing a path from a point external to the body to the tumor site. The source wire includes a thin continuous cylindrical flexible elongate stainless steel tube having encased therein a backbone wire running from its proximal end to a point short of its distal end to strengthen and enhance its flexibility, a cylindrical radioactive core adjacent to the distal end in abutting relation to the backbone wire, and a cylindrical plug at the distal end in abutting relation to the other end of the core, with the backbone wire, core and plug being tightly secured within the tube and the tube being securely enclosed about the plug with a tapered tip portion formed at that point. The source wire has an overall diameter sized to permit ease of movement through the catheter in advancement to the tumor site for the radiation treatment and to allow its retraction through the catheter from the point external to the body. The exterior surface of the tube is gold plated from its tip to the far end of the portion overlying the core. The source wire has an extremely small diameter (under 0.7 mm) and is sufficiently flexible that even in high radioactive dose sizes it is capable of passing through very narrow and even kinked catheters, making it useful for treating inoperable tumors such as common bile duct pancreatic cancer.

Hoffman et al., U.S. Pat. No. 4,693,237, describes marker members of radiopaque material in the form of bands each of a different geometric configuration which are sutured to the point at which a surgical graft to a blood vessel is made as in a coronary bypass operation. These ring or other shaped radiopaque members provide markers identifying the exact coronary blood vessel that the graft will lead to, each geometrical shape identifying a different coronary vessel bypassed, thus facilitating bypass graft catherization by identifying the entry point of any specific bypass graft.

Lam et al., 0 679 372 A2, teaches a radiopaque marker associated with a stent which is adapted to be implanted into a body lumen of a patient to maintain the patency thereof and a convenient and accurate method for affixing the radiopaque marker to the stent. The radiopaque marker defining an acceptable profile and capable of facilitating, under fluoroscopy, the identification of the position, diameter and length of a stent without obscuring the lesion being repaired and without impeding the deformation of an expendable stent.

Bahler et al., EP 0 146 699 A1, teaches implants consisting of contrast body and anchoring body fixed positionally secure in the bone with the aid of a structure of the anchoring body and thus form, in the bone, immovable reference points for the measurement of x-ray pictures.

Ellis, U.S. Pat. No. 5,636,255, describes a method and system for correlating accuracy of computer tomography (CT) image resolution. Small radio-opaque markers having a diameter less than one slice width of a CT scan are embedded in the object, such as a bony skeletal member, to be measured, the object is then CT scanned so that the radio-opaque markers appear in at least two slices of the scan. The markers are also physically located by detecting them with a sensor, such as a positioning pointer. Also described is one form of marker comprising a tantalum sphere mounted in a ceramic, preferably alumina, pin.

Jensen et al., U.S. Pat. No. 6,181,960 B1, teaches a radiographic marker that is used to indicate a biopsy site and entry path. The marker has an arrow shape configuration with a shaft and a pair of limbs extending from the shaft at an angle of less than about 90 degrees. The tip of the arrow indicates the biopsy site and the shaft indicates the said entry path. The marker preferably is a single piece of wire, having a diameter of less than 0.010 inches, folded to four sections, to form the limbs and shaft of the arrow. Fibers can be affixed to the shaft to cause the marker to fibrose within the tissue. An introducing device, having a body and a hub, is used to insert the marker. A cannula, dimensioned to receive the body and hub of the introducing device, has a pair of receiving channels within the interior of the body to receive the limbs of the marker.

Jones, U.S. Pat. No. 4,202,349, describes a radiopaque blood vessel marker for attachment to the side wall portions of a blood vessel during, for example, a coronary by-pass operation. The markers in the preferred embodiment are flattened, oval-shaped radiopaque discs which are attached to the outer peripheral wall portion of the blood vessel at one hundred eighty degrees (180.degree.) with respect to one another (See FIG. 3). Each radiopaque marker can be comprised of a central imbedded element of radiopaque material such as tantilum which is surrounded by a suitable plastic or like resinous material which is inert and acceptable for use within the human body. During a coronary by-pass, for example, these markers could be attached by suturing or like means to the vein graft which is itself sutured into its new position during the by-pass operation. A fluoroscopic examination by a radiologist would reveal a desirable pulsation of the graft vessel in the form of the two attached markers as the radiopaque markers will constantly move (in and out) with respect to one another. Each marker is attached to the undulating wall portion of the vessel which is constantly moved when blood flow is passing through the graft as is desirable. In the event that complications arise, and the graft becomes clotted (stopping the flow of blood therethrough), a fluoroscopic examination will reveal that the radiopaque vessel markers do not move in and out with respect to one another but rather are stationary indicating a lack of undulation and a corresponding lack of blood flow.

Elliot et al., U.S. Pat. No. 4,041,931, relates to split ring markers fabricated in whole or in part from a radiopaque material, usually metal, having the terminal ends thereof and a medial portion formed to define eyelets by means of which said marker can be sutured to the tissue at the sight of an anastomosis to provide a visual indication of its location when examined fluoroscopically.

Foerster et al., U.S. Pat. No. 5,902,310, teaches an implantable marking device which is designed to percutaneously deliver permanent markers to desired tissue locations within a patient's body, even if the desired locations are laterally disposed relative to the distal end of the delivery device, as is the case for conduit or cavity walls. This provides several advantages to the physician in diagnosis and management of tissue abnormalities, such as a means of localization of a tissue abnormality for follow-up surgical treatment, and a means of tissue abnormality site identification for purposes of ongoing diagnostic follow-up. In one preferred construction, a radiographic clip is configured in the form of a surgical staple. A disposable tissue marker applier, which comprises a flexible tube, pull wire, and squeeze handle, is employed to advance and deploy the clip to a desired tissue location. Either a flexible or a rigid introducer is also provided for providing access to the site to be marked.

Morris, U.S. Pat. No. 4,331,654, describes a drug carrier formulation consisting of magnetically-localizable, biodegradable lipid microspheres.

Granov et al., U.S. Pat. No. 5,236,410, describes a method of treatment of a tumor comprising the steps of catheterization of the arterial vessel that feeds the tumor, and transcatheter administration of a suspension of magnetically hard ferromagnetic material in an oil solution of an oil-soluble antitumor substance with simultaneous application of local magnetic field onto the area of the tumor. After 1–3 days the tumor is subjected to ultrahigh radio frequency electromagnetic field or ultrasonic waves to produce heating of the tumor tissue to the temperature of 43.0.degree.–43.5.degree. C. for a period of 5–45 minutes.

Tournier et al., U.S. Pat. No. 5,668,490, teaches suspensions of either echogenic or magnetic particles in aqueous bioadhesive carriers that effectively improve imaging by echography, respectively NMRI, of the digestive tract. Affinity of the compositions for the gastric mucosa can be adapted to the needs by appropriately selecting the carrier in function to inherent bioadhesive capacity: this technique leads to improved visualization of selected portions of the lumen.

Additional patents of interest include Dowlatshahi, U.S. Pat. No. 5,853,366, which describes a marker element which is made of radiopaque material and includes at least two leg portions of approximately equal length connected at an angle relative to each other to form a generally V-shaped resilient member that is capable of being positioned wholly within the body of a patient. A localizing device and method using the marker element for marking a tissue mass of interest are also provided. The device and method include an elongate guide member, such as a cannula, having a first end that is inserted into the body so as to be directed toward a position proximate the tissue mass of interest and an opposite second end that extends from the body. A guide path extends between the first end and the second end of the guide member. The marker element is introduced into the second end of the guide member using a marker element dispenser and then urged along the guide path using a stylet or similar prodding member.

The marker element collapses to a reduced size while being urged along the guide path, and substantially resumes its original V-shape upon discharge from the guide member so as to remain in a fixed position wholly within the body without irritating or traumatizing the surrounding tissue. A plurality of marker elements may be positioned in a similar manner to mark the tissue mass of interest.

Wichterle et al., U.S. Pat. No. 3,818,894, teaches an implant for surgical purposes which is especially useful for the operative treatment of the afflicted vocal cords, as well as to the method for its production. The implant is made from water-swellable and physiologically inert material, such as a synthetic cross-linked hydrophilic gel, and has in a dry state, when it is ready for use in an operation, the shape of a straight or bent stick provided with a sharp, pointed tip. The implant body except the tip may contain physiologically inert plasticizers.

Tucci, U.S. Pat. No. 4,545,367, teaches a detachable balloon catheter assembly which comprises a balloon and sealing valve assembly including a sealing valve being formed of a resilient material having an elongate passageway extending therethrough and being mounted in a sleeve, an inflatable balloon having a mouth portion which is bonded to the sealing valve, and a small diameter cannula having a distal end which extends through the passageway in the sealing valve. The small diameter cannula includes a connector terminal on the proximal end which is adapted to be coupled to a source of fluid pressure. The passageway in the sealing valve takes the form of an elongate slit prior to insertion of the small diameter cannula through the passageway, and upon insertion of the cannula through the passageway, the passageway takes the form of a cylindrical aperture which is in fluid-tight engagement with the outer surface of the cannula while allowing the cannula to easily slide through the passageway. When the balloon is inflated to a desired size, the cannula may be withdrawn from the passageway in the sealing valve thereby causing the passageway to revert to the slit configuration in order to provide a fluid-tight seal for the inflated balloon. In one embodiment, a piston is mounted on the small diameter cannula and an aperture extends through the side wall of the cannula so that a burst of fluid pressure may be applied to the piston causing it to be driven away from the sealing valve to drive the cannula out of engagement with the sealing valve for detachment of the cannula from the inflated sealed balloon.

Ahmed, U.S. Pat. No. 4,647,480, teaches a curing of autodeposited coatings by treatment with water or steam including a solute.

Barlow et al., U.S. Pat. No. 5,422,730, describes a method and apparatus for optical detection and imaging of regional circulatory flow in biological tissues for research purposes. An animal or plant organ is perfused with a saline suspension of colored and/or fluorescent microspheres. The organ is excised and fixed in the form of a specimen block for mounting in a microtome or other suitable apparatus. Under automatic control of a microcomputer equipped with a frame grabber, a surface layer of the block is removed, the resulting new exposed surface of the block receives a flash of illumination from a light source, and light reflected by colored microspheres or, alternatively, light emitted by fluorescent microspheres, is detected by a CCD video camera aimed at the block. Also under microcomputer control, light filters having suitable light bandpasses are interposed between the light sources and the block, and between the block and the camera. Video signals are converted by the microcomputer into position coordinates with associated optical intensities from which regional circulatory flow is computed and displayed on a monitor.

Swartz et al., U.S. Pat. No. 5,494,030, teaches apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1–2 GHz range. The EPR spectra is then measured at the biological system to determine oxygen concentration. The EPR spectra is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively.

Leeb et al., U.S. Pat. No. 5,643,246, describes a system for remotely inducing a phase transition in a gel. The system includes a gel capable of volume change in response to an environmental stimulus, a seed material in contact with the gel, and generating a time-varying magnetic or a time-varying electric or electromagnetic field in the proximity of the gel to produce the environmental stimulus. In a preferred embodiment, the environmental stimulus is temperature.

Klaveness et al., U.S. Pat. No. 5,676,925, describes contrast agents comprising gas-containing or gas-generating polymer microparticles and/or microballoons, in which the polymer is a biodegradable polymer containing units of formula —$(O)_m$—CO—O—C($R^1 R^2$)—O—CO—$(O)_n$ —(wherein $R^1$ and $R^2$ each represent hydrogen or a carbon-attached monovalent organic group or together form a carbon-attached divalent organic group, and m and n are each independently zero or one) may be used in diagnostic applications such as ultrasound and MR imaging.

Miller et al., 0 481 685 A1, teaches a medical device for localizing a non-palpable breast lesion. The device includes a tubular introducer needle and a wire guide positioned therein for inserting into a breast to the site of the lesion.

Chapelon et al., WO 93/14712, teaches an device for treating a lesion that includes a locating device that is operably connected to a treatment device. The locating device is capable of computing the position of the lesion relative to the treatment device.

Foerster et al., WO 96/08208 A1, teaches a device used to later identify the location of a biopsy or surgery.

Foerster et al., WO 98/06346, describes an implantable marking device which is designed to percutaneously deliver permanent markers to desired tissue locations within a patient's body, even if the desired locations are laterally deposed relative to the distal end of the delivery device, as is the case for conduit or cavity walls.

The prior art teaches various implantable markers. However, the prior art does not teach an implantable ultrasound imaging marker constructed of an ultrasound resonant material and having a resonant pocket. The prior art also does not teach a metallic resonant layer that functions to amplify the signal to an ultrasound machine. The present invention fulfills these needs and provides further related advantages as described in the following summary.

SUMMARY OF THE INVENTION

The present invention teaches certain benefits in construction and use which give rise to the objectives described below.

The present invention provides an ultrasound imaging marker for marking a location in a mammalian body. The ultrasound imaging marker has a marker body that is constructed of an ultrasound resonant material and that includes a resonant pocket. The marker body includes an interior surface and preferably an angled surface. The resonant pocket provides a feature that is easily visible to the ultrasound device. The interior surface is preferably coated with a metallic resonant layer such as alumina or gold. The angled surface bounds the interior surface and connects the interior surface with the perimeter lip. The angled surface is preferably disposed on a plane that is preferably at an angle of approximately 126 degrees from the angle of the interior surface. The ultrasound imaging marker is preferably used in conjunction with an insertion device for inserting the ultrasound imaging marker adjacent the location.

A primary objective of the present invention is to provide a surgical marking system, including an ultrasound imaging marker, having advantages not taught by the prior art.

Another objective is to provide an ultrasound imaging marker that enables accurate marking and easy detection of a location in a mammalian body using an ultrasound device.

A further objective is to provide an implantable ultrasound imaging marker constructed of an ultrasound resonant material and having a resonant pocket that provides a return signal to the ultrasound device.

A further objective is to provide an ultrasound imaging marker having a metallic resonant layer on an interior surface of the resonant pocket to amplify the signal to an ultrasound device.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

The above-described drawing figures illustrate the invention, an ultrasound imaging marker 10 useful for marking a location 11 in a mammalian body 12. The ultrasound imaging marker 10, shown in FIGS. 1–7, is preferably used as part of a surgical marking system, shown in FIGS. 8–11, that includes an insertion device 60 for positioning the ultrasound imaging marker 10 adjacent the location 11, as shown in FIG. 11.

Figures 10, 11:
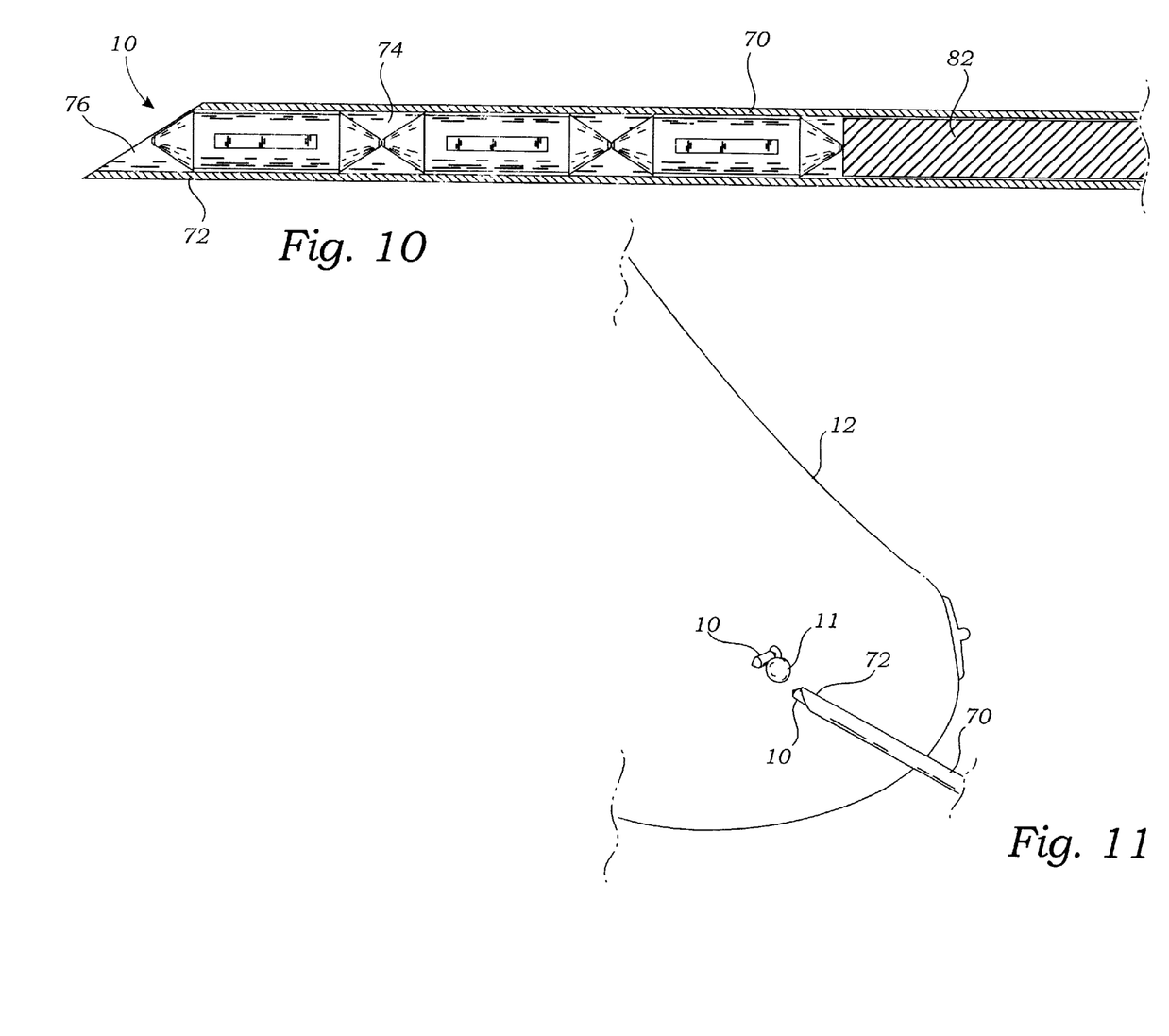
FIG. 10 is a side elevational sectional view of a cannula of the insertion device illustrating how three ultrasound imaging markers can be positioned within the insertion device.
FIG. 11 is a side elevational sectional view of the insertion device being used to insert two of the ultrasound imaging markers adjacent a location, a tumor, in the mammalian body.
Figure 12:
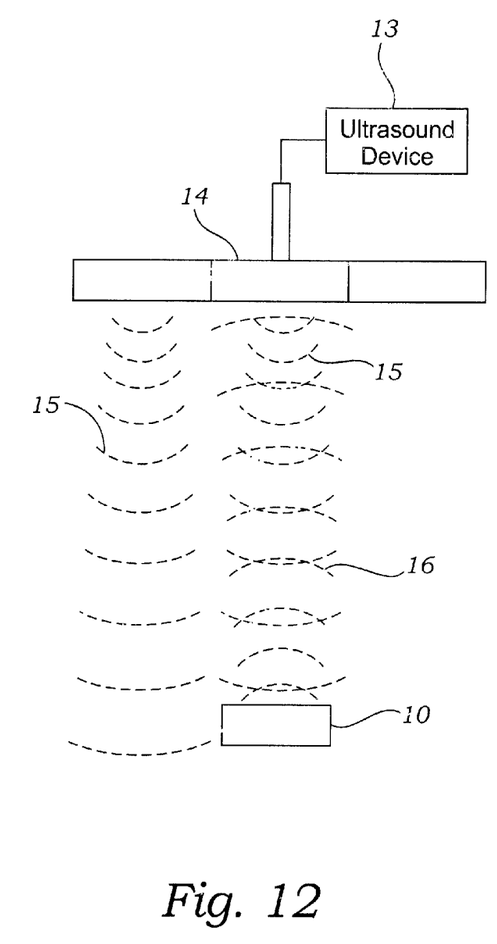
FIG. 12 is a side elevational view illustrating how a transducer of an ultrasound device is used to project an ultrasound wave onto the ultrasound imaging marker, and how the ultrasound imaging marker generates reflected waves that are detected by the transducer.
Figure 13:
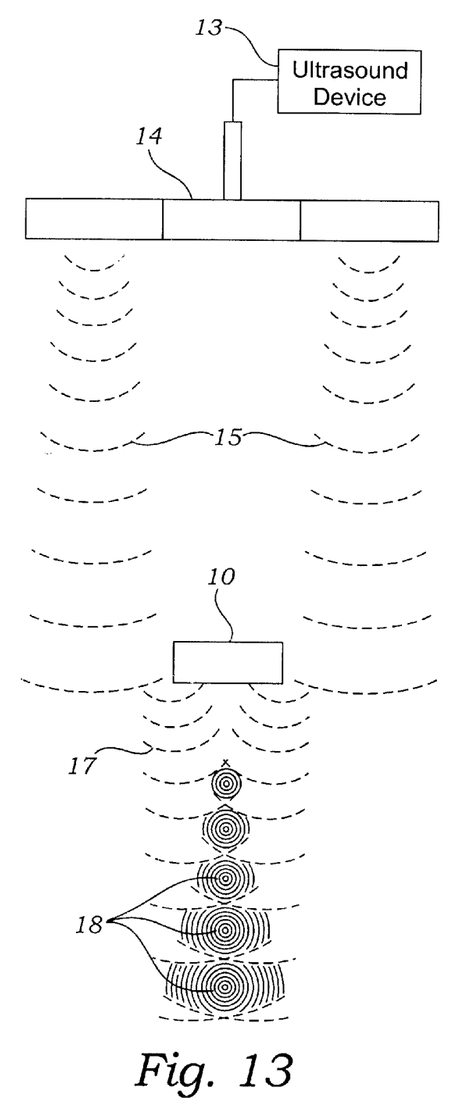
FIG. 13 is a side elevational view illustrating how the ultrasound imaging marker generates reflected and refracted waves that form a moire pattern that is detected by the transducer.

In one embodiment, shown in FIG. 10, the surgical marking system includes three ultrasound imaging markers 10; however, for clarity we will describe the ultrasound imaging marker 10 in the singular. As shown in FIGS. 12–13, the ultrasound imaging marker 10 is designed for use in conjunction with ultrasound device 13 having a transducer 14. The ultrasound device 13 typically operates in the 3.5–20.0 megahertz range.

As shown in FIGS. 1–7, the ultrasound imaging marker 10 includes a marker body 20 constructed of an ultrasound resonant material such as plastic, vinyl, silicon, glass, copolymer, or equivalent material. In one embodiment, the ultrasound resonant material is constructed of bioabsorbable polymer of similar material. The marker body 20 has an interior surface 22 and an exterior surface 24. The interior surface 22 defines a resonant pocket 26. A metallic resonant layer 28 covers at least a portion of the interior surface 22. The combination of the resonant pocket 26 and the metallic resonant layer 28 function to reflect, refract, or deflect the ultrasound waves 15, as shown in FIGS. 12–13, thereby making the location 11 readily apparent to a search by the ultrasound device 13. This construction makes the ultrasound imaging marker 10 an effective marker despite its small size, which is preferably less than 5 mm in length.

Figure 1:
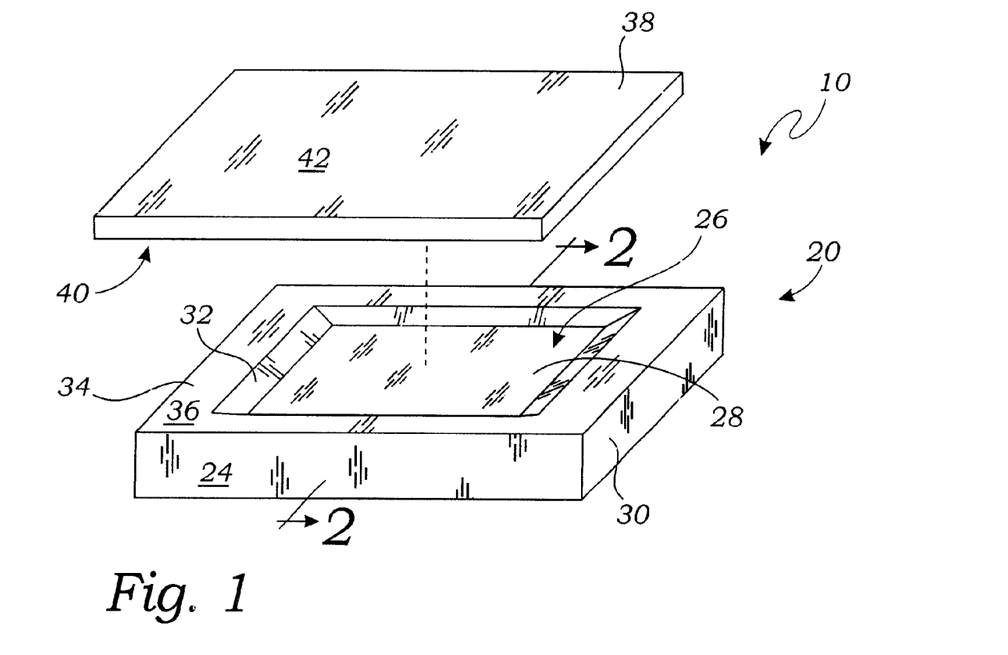
FIG. 1 is an exploded perspective view of a first embodiment of an ultrasound imaging marker.
Figure 2:
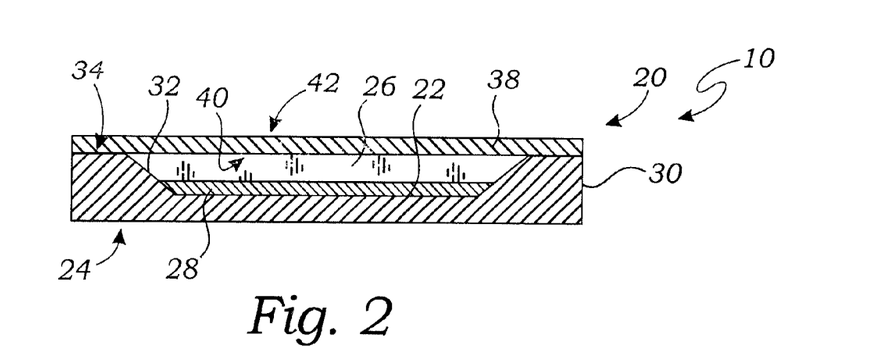
FIG. 2 is a sectional view thereof taken along line 2—2 in FIG. 1.
Figure 3:
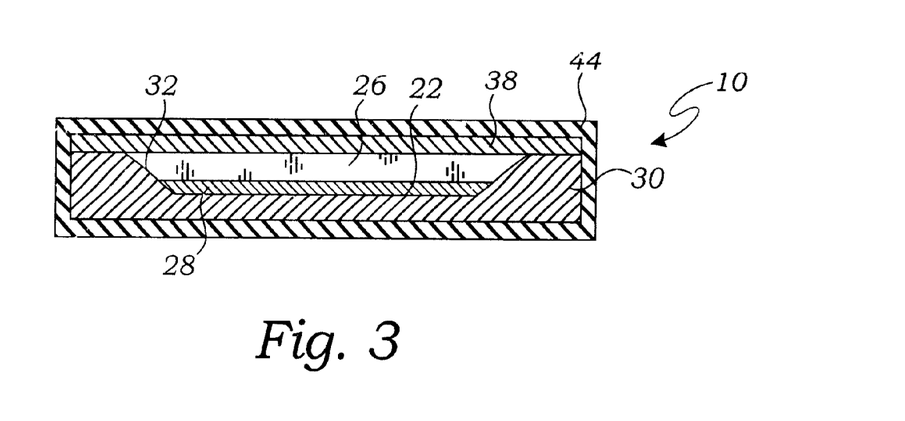
FIG. 3 is a sectional view thereof illustrating the addition of a biocompatible coating around the ultrasound imaging marker.

In a first embodiment, as shown in FIGS. 1–3, the marker body 20 is constructed of a marker base 30 and a cap 38. The marker base 30 has an angled surface 32, a perimeter lip 34, and an exterior surface 24 in addition to the interior surface 22. The perimeter lip 34 defines an opening to the resonant pocket 26, the resonant pocket 26 being bounded by the interior surface 22 and the angled surface 32. The cap 38 functions to seal the resonant pocket 26.

To enhance the visibility of the resonant pocket 26, the interior surface 22 is preferably generally planar, although this is not required for the function of the ultrasound imaging marker 10. Due to the difference in the echogenicity of the air in the resonant pocket 26 and the ultrasound resonant material of the marker base 30, the interior surface 22 functions to reflect and refract ultrasound waves 15. As shown in FIG. 12, reflected waves 16 from the ultrasound imaging marker 10 can be detected using a transducer 14 of the ultrasound device 13.

As shown in FIG. 1, the angled surface 32 bounds the interior surface 22 and connects the interior surface 22 with the perimeter lip 34. The angled surface 32 is preferably disposed on a plane that is at an angle of between 120–140 degrees with respect to the plane of the interior surface 22, more preferably at an angle of between 123–130 degrees, and most preferably at an angle of approximately 126 degrees. As shown in FIG. 13, the angled surface 32 functions to refract the ultrasound waves 15 to form refracted waves 17. The refracted waves 17 form a moiré pattern 18 that is readily discernable on the ultrasound device 13. The moiré pattern 18, sometimes known as a "waterfall effect," facilitates locating the ultrasound imaging marker 10 using the ultrasound device 13.

As shown in FIGS. 1–2, the cap 38 has an inner cap surface 40 and an exterior cap surface 42. The perimeter lip 34 further has a lip surface 36. The lip surface 36 is preferably disposed on a plane that is generally parallel to the plane of the interior surface 22. The inner cap surface 40 is mounted on the perimeter lip 34 and bonded to the lip surface 36 of the marker base 30 to close the opening of the resonant pocket 26.

In one embodiment, in which the marker base 30 and the cap 38 are made of silicon, the silicon components naturally bond together so that the inner cap surface 40 adheres to the lip surface 36 of the marker base 30. In alternative embodiments, an adhesive can be used to bond the inner cap surface 40 and the lip surface 36. In the one embodiment in which the marker base 30 is made of silicon, the interior surface 22 is preferably etched from a silicon wafer using KOH etching, a technique well known in the art and therefore not described in greater detail herein.

As shown in FIG. 3, the cap 38 and the marker base 30 are preferably coated with a biocompatible coating 44 or sealant, such as paralyne, to further prevent leakage into the resonant pocket 26. The biocompatible coating 44 can also be used to coat the cap 38 and the marker base 30 if either of the above elements are not suitably biocompatible. Since the marker body 20 is preferably biocompatible, however, the biocompatible coating 44 is not generally required for biocompatibility.

Figure 4:
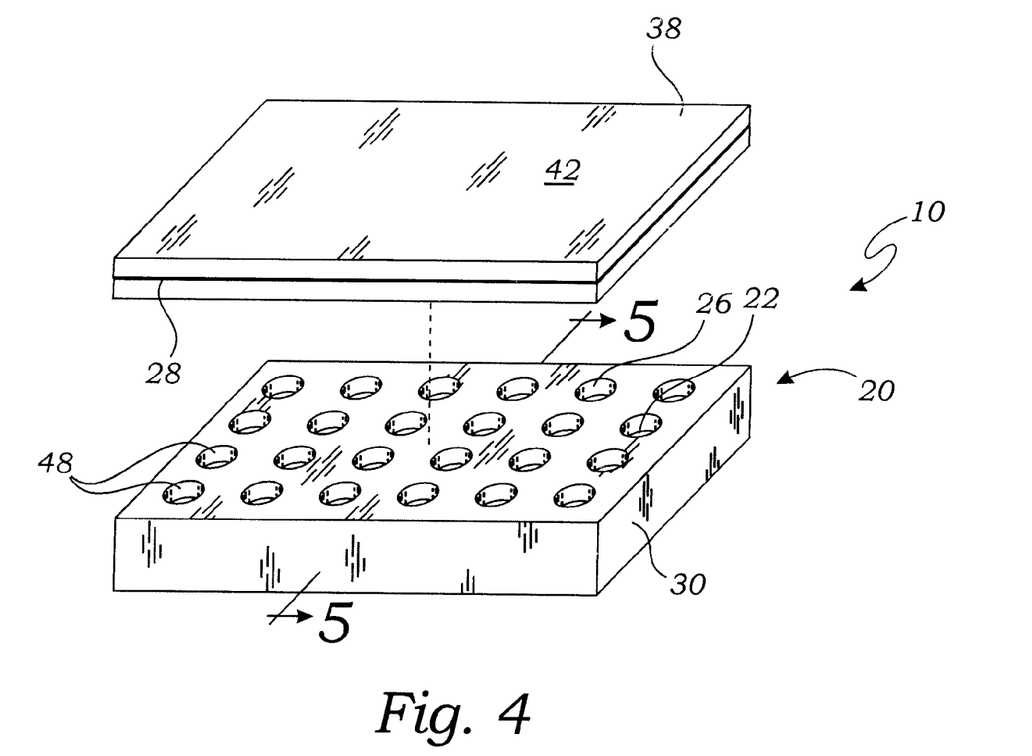
FIG. 4 is an exploded perspective view of a second embodiment of the ultrasound imaging marker.
Figure 5:
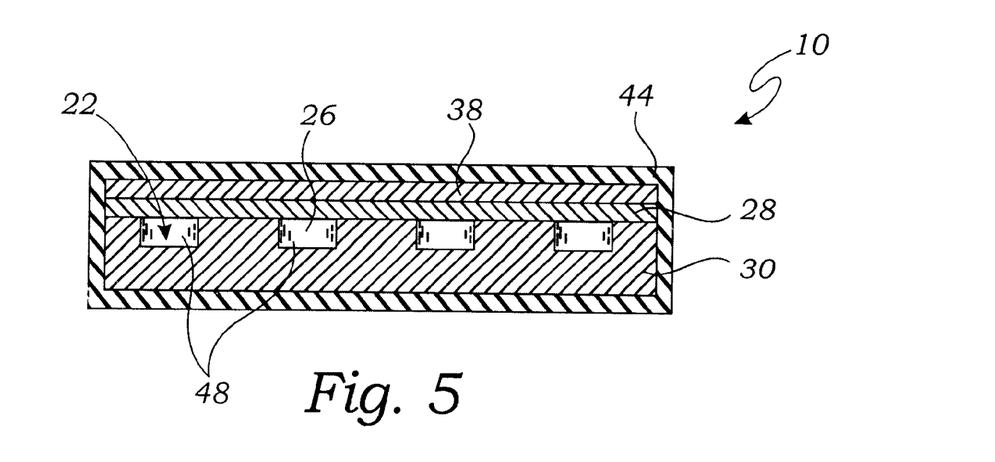
FIG. 5 is a sectional view thereof taken along line 5—5 in FIG. 4, the view illustrating the inclusion of the biocompatible coating as shown in FIG. 3.

In one embodiment, shown in FIG. 2, the interior surface 22 is preferably coated with a metallic resonant layer 28 such as alumina or gold. The metallic resonant layer 28 can be formed by sputtering alumina, which is inexpensive, onto the interior surface 22; however, gold or other metals can also be used, especially in applications where higher costs are not a barrier. Also, other deposition or layering techniques can be used by those skilled in the art, and such alternative techniques should be considered within the scope of the present invention. In addition to enhancing the ultrasound signal, the metallic resonant layer 28 serves to assist in the identification of the CHIP when using x-ray or similar In a second embodiment, as shown in FIGS. 4–5, the interior surface 22 is formed by a plurality of bores 48. The plurality of bores 48 are preferably evenly spaced in a grid pattern, and each of the plurality of bores 48 is preferably between 50–150 microns deep, more preferably between 80–120 microns deep, and most preferably approximately 100 microns deep. In this embodiment, the metallic resonant layer 28 is preferably formed on the interior cap surface of the cap 38 so that when the cap 38 is bonded to the marker base 30, the metallic resonant layer 28 is properly positioned as part of the resonant pocket 26. While the two embodiments described illustrate the preferred methods of forming the resonant pocket 26, alternative arrangements can be devised by those skilled in the art, and should be considered within the scope of the claimed invention.

Figure 5A:
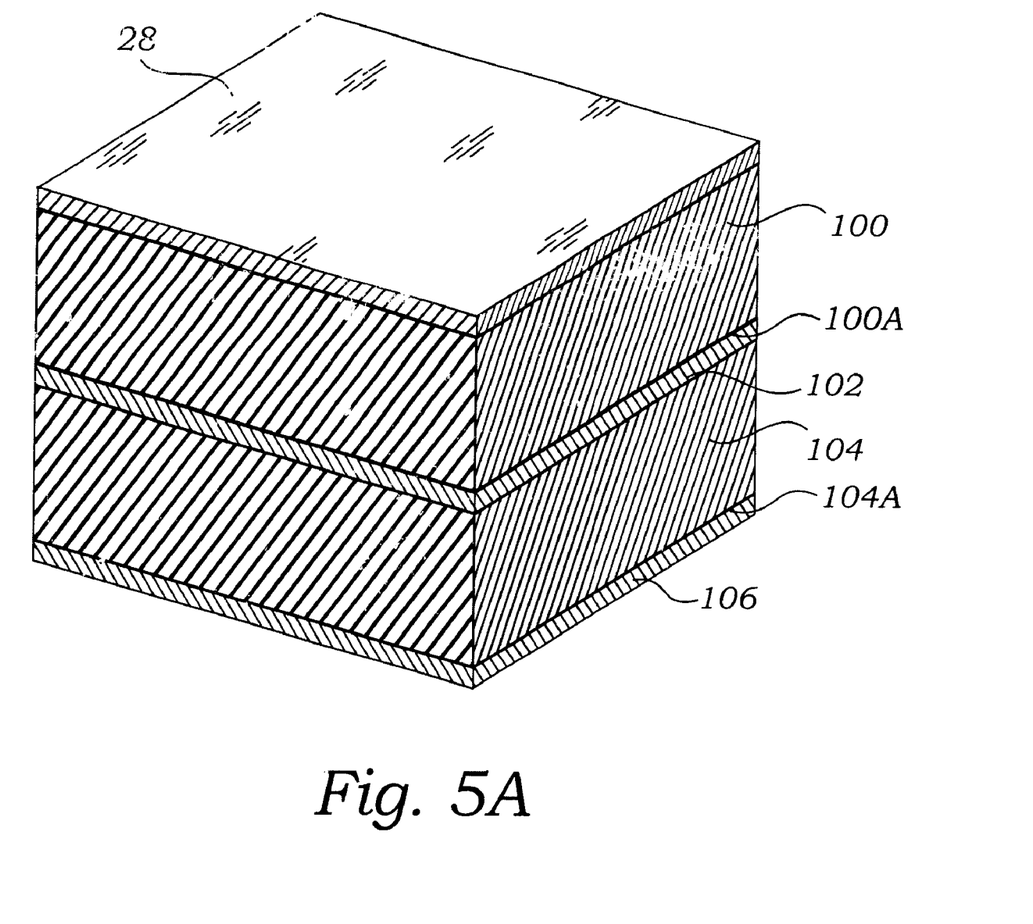
FIG. 5A is a sectional view of a third embodiment of the ultrasound imaging marker.

In another embodiment, as shown in FIG. 5A, the ultrasound imaging marker 10 includes a marker body 20 constructed of a first silicon layer 100 coated upon one side with the metallic resonant layer 28, and upon the opposing side having a first silicon oxide layer 102. In one embodiment, the marker body 20 further includes a second silicon layer 104 that is sandwiched between the first silicon oxide layer 102 and a second silicon oxide layer 106. In this embodiment, the metallic resonant layer 28 includes both alumina and gold. Each of the first and second silicon layers 100 and 104 are etched using a well known etching technique such as chemical (KOH) etching or similar method, to form roughened surfaces 100A and 104A, that have various small pits and irregularities. Upon exposure to air, the roughened surfaces 100A and 104A form the first and second silicon oxide layers 102 and 106. It has been found that merely providing a roughened surface serves to form the resonant pocket 26 without specifically etching the plurality of bores 48. While this embodiment is not as effective as the technique described above, it is still fairly effective and much cheaper to manufacture. The marker body 20 in this embodiment is typically about 1 mm wide and 0.5 mm thick, although the size can vary depending upon the requirements of the user.

Figure 6:
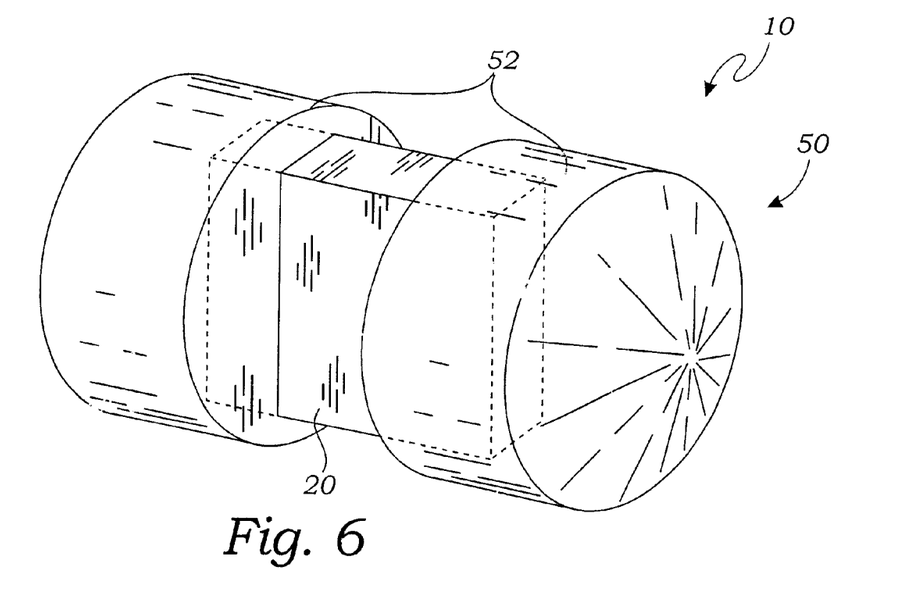
FIG. 6 is a perspective view of the ultrasound imaging marker including a pair of positioning end caps that function to prevent migration of the ultrasound imaging marker within a mammalian body.
Figure 7:
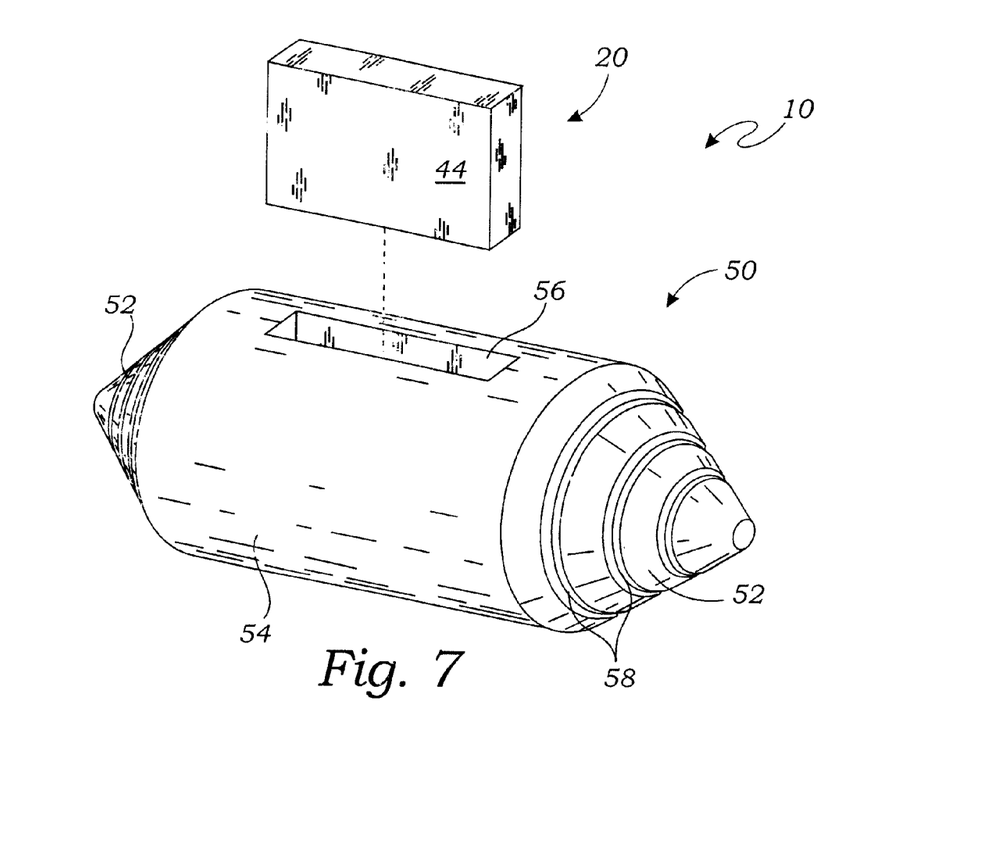
FIG. 7 is a perspective view of the ultrasound imaging marker being inserted into a slot of a central body, the central body having a pair of positioning end caps that likewise function to prevent migration of the ultrasound imaging marker.

The ultrasound imaging marker 10 is preferably associated with a means for preventing migration 50 of the ultrasound imaging marker 10 within the mammalian body 12. As shown in FIGS. 6–7, the means for preventing migration 50 includes at least one positioning end cap 52 operably attached to the ultrasound imaging marker 10. The at least one positioning end cap 52 functions to properly position the ultrasound imaging marker 10 within soft tissue of the mammalian body 12 and prevent migration of the ultrasound imaging marker 10 therein. The at least one positioning end cap 52 is preferably constructed of polypropylene or similar material and functions to prevent migration of the ultrasound imaging marker 10.

In a first embodiment, as shown in FIG. 6, the outer shell includes a pair of positioning end caps 52 that are each attached to an end of the ultrasound imaging marker 10 using a frictional fit and preferably an adhesive. Each of the pair of positioning end caps 52 is preferably shaped and constructed to prevent migration of the ultrasound imaging marker 10 within the mammalian body 12.

In a second embodiment, as shown in FIG. 7, the ultrasound imaging marker 10 is positioned within a central body 54 having a slot 56 shaped to receive the ultrasound imaging marker 10. The central body 54 is integral with the at least one positioning end cap 52 and also constructed of a biocompatible material, preferably also polypropylene, polyethylene, or similar material. The at least one positioning end cap 52 includes at least one concentric furrow 58 that helps stabilize the ultrasound imaging marker 10 within the mammalian body 12.

Figure 7A:
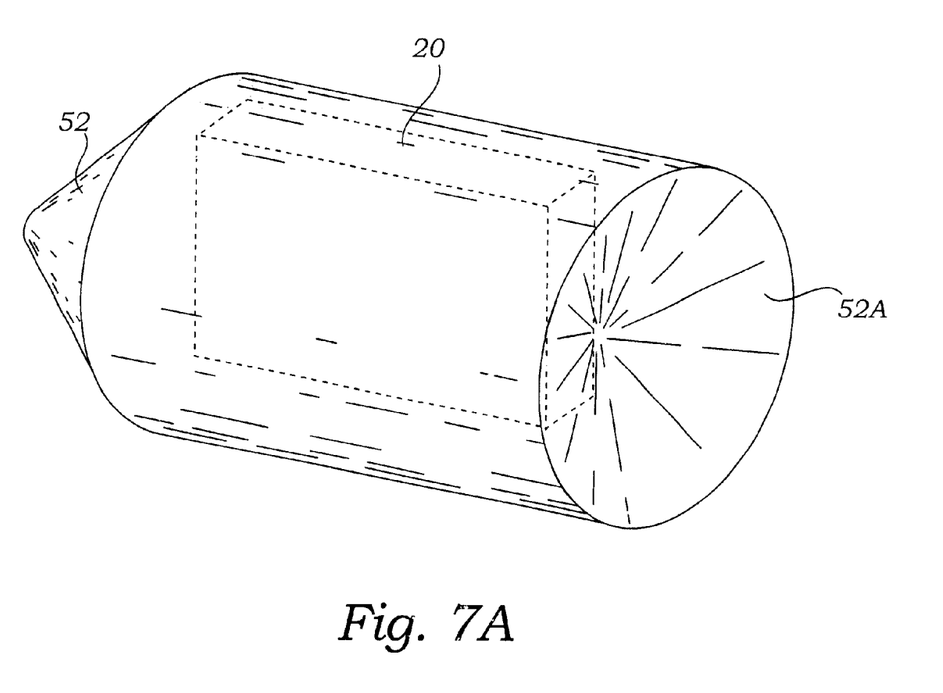
FIG. 7A is a perspective view of the ultrasound imaging marker including another embodiment of the pair of positioning end caps.
Figure 8:
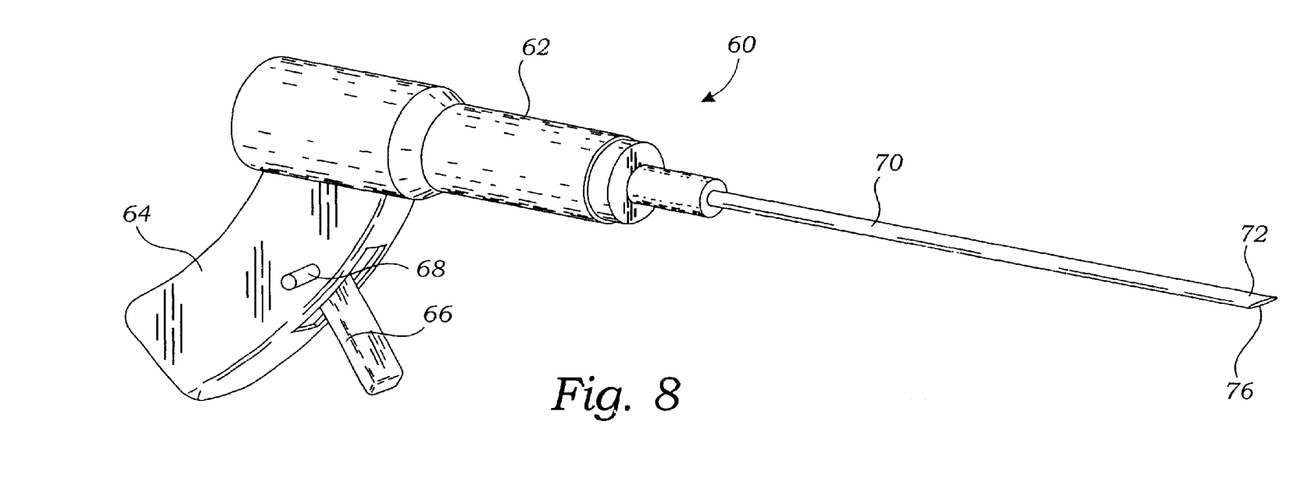
FIG. 8 is a perspective view of an insertion device adapted for use with the ultrasound imaging marker.

In a third embodiment, as shown in FIG. 7A, the ultrasound imaging marker 10 is molded within the central body 54. In this embodiment, the central body 54 includes one end cap 52 that protrudes outward, and an indented end cap 52A. The indented end cap 52A serves the same purpose as the other end cap 52, but the indented shape allows the ultrasound imaging markers 10 to be packed more tightly end to end.

While the preferred embodiment has been described, those skilled in the art can devise alternative means for preventing migration 50 of the ultrasound imaging marker 10 within the mammalian body 12. Alternative examples include, but are not limited to, attaching the ultrasound imaging marker 10 to a fixed body such as a prosthesis, staple, or other body, or to a fixed portion of the mammalian body 12, such as a bone. The ultrasound imaging marker 10 can also be built directly into a prosthesis, screw, or other implant before the implant is placed in the mammalian body 12. The ultrasound imaging marker 10 can also be sewn or stapled into position. The ultrasound imaging marker 10 can also be associated with a surgical instrument (not shown) so that the surgical instrument can be viewed using the ultrasound device 13. Those skilled in the art can devise alternative mechanisms or techniques for fastening the ultrasound imaging marker 10 into its position adjacent to the location 11 being marked.

The surgical marking system preferably includes the insertion device 60 for inserting the ultrasound imaging marker 10 adjacent the location 11 in the mammalian body 12. The insertion device 60, shown in FIG. 8, preferably includes an insertion device body 62 and a hand grip 64 that extends downwardly from the insertion device body 62. A trigger 66 extends downwardly from the insertion device body 62 in front of the hand grip 64 and is pivotally attached to the hand grip 64 with a pivot pin 68 for operative movement, as described below. Obviously, the term trigger 66 is not limited to the specific embodiment shown, but includes equivalent mechanisms such as buttons, electromechanical mechanisms, and other means of triggering the insertion device 60 that can be devised by those skilled in the art.

Figure 9:
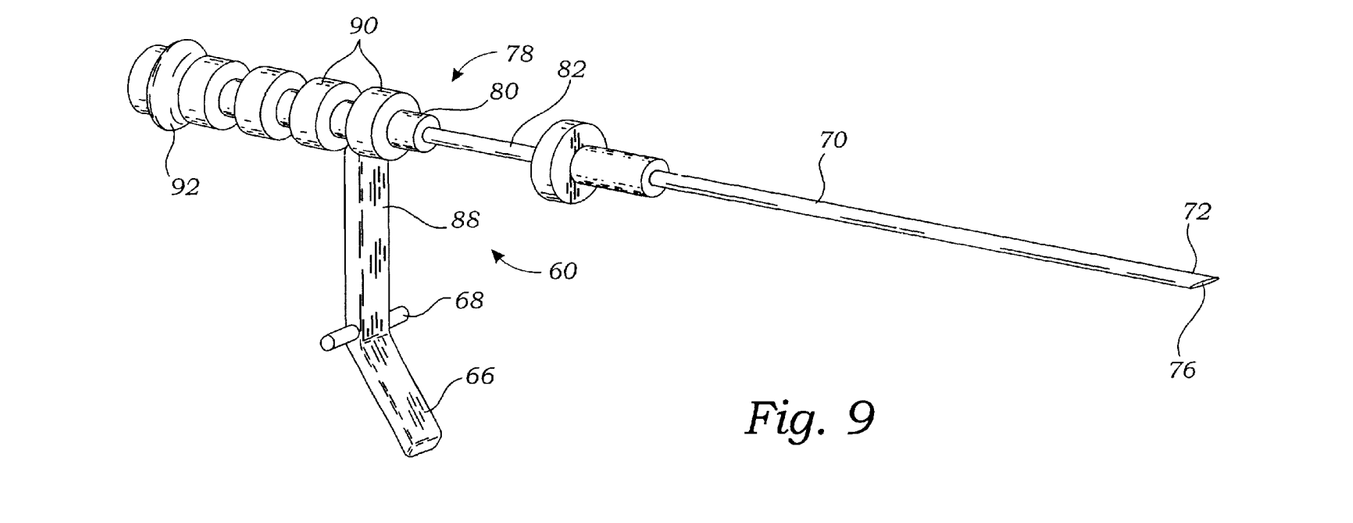
FIG. 9 is a perspective view of an ejection device within the insertion device for ejecting the ultrasound imaging marker.

As shown in FIGS. 9–10, the insertion device 60 preferably has a cannula 70 with an insertion tip 72 for inserting the ultrasound imaging marker 10. The insertion tip 72 has an interior cannula chamber 74 shaped to receive the ultrasound imaging marker 10 and dispense the ultrasound imaging marker 10 through a cannula opening 76 of the insertion tip 72 into the mammalian body 12. In the preferred embodiment, as shown in FIG. 10, the interior cannula chamber 74 is shaped to receive three of the ultrasound imaging markers 10; however, the interior cannula chamber 74 can be adapted to hold any number of the ultrasound imaging markers 10, depending upon the needs of the users.

The insertion device 60 further includes a means for ejecting 78 one of the ultrasound imaging markers 10 upon actuation of the trigger 66. In one embodiment, as shown in FIG. 9, the means for ejecting 78 includes an elongate shaft 80 attached to a plunger 82 that is operably positioned within the cannula 70. When the trigger 66 is squeezed towards the hand grip 64, the trigger 66 pivots about the pivot pin 68 so that an upper portion 88 of the trigger 66 contacts one of a plurality of engagement ridges 90 of the elongate shaft 80. The plurality of engagement ridges 90 are spaced approximately the length of the ultrasound imaging markers 10 so that advancing the shaft the length of one of the plurality of engagement ridges 90 ejects one of the ultrasound imaging devices. The trigger 66 is designed to remain in contact with the engagement ridge 90, and thereby advance the shaft, until the plunger 82 has moved far enough to eject the one of the ultrasound imaging markers 10. The shaft further includes friction ring 92, preferably constructed of rubber or similar material, which frictionally contacts the insertion device body 62 and prevents the shaft from retracting when the trigger 66 pivots back to the original position. Once the trigger 66 has returned to the original position, the upper portion 88 contacts the next of the plurality of engagement ridges 90, ready to advance the plunger 82 again and eject another of the ultrasound imaging markers 10. While the mechanism described is one possible preferred, alternative structures can also be used. In one alternative embodiment, in which the insertion device 60 holds only one ultrasound imaging marker 10, a simple plunger mechanism can be used without the need for the more complex mechanism described.

Also, while the embodiment described includes a cannula 70 that is rigid and that includes a rigid connection, the plunger 82 and elongate shaft 80, it is also possible to utilize a flexible actuation mechanism (not shown) that enables the surgeon to direct the insertion tip 72 along a convoluted route to the location 11. Such an embodiment is useful for certain surgical procedures, such as arthroscopic surgery, that often do not provide a direct route to the location 11. Such flexible actuation mechanisms are well known in the art, and therefore not described in greater detail herein.

The invention further includes a method for marking a location 11 in a mammalian body 12 using the above-described surgical marking system. The ultrasound imaging marker 10 is provided operably positioned within the insertion device 60 and the cannula 70 of the insertion device 60 is inserted into the mammalian body 12 until the insertion tip 72 is adjacent the location 11. Finally, the ultrasound imaging marker 10 is ejected, as described above, so that it remains adjacent the location 11.

At a later time, the surgeon can use the ultrasound device 13 to check the location 11 of the ultrasound imaging marker 10. The transducer 14 is operably connected to the ultrasound device 13 and placed over the location 11 and the ultrasound waves 15 are directed at the ultrasound imaging marker 10, which is plainly visible to the ultrasound device 13, as described above. This enables the surgeon to periodically check the location 11 of the ultrasound imaging marker 10 to see if the ultrasound imaging marker 10 has moved, or as a locator to direct future surgical procedures.

In one example, the ultrasound imaging marker 10 can be used during surgery to remove a tumor from a breast. In this example, when a biopsy is removed from the suspected tumor, the ultrasound imaging marker 10 can be positioned adjacent the edge of the suspected tumor, or a plurality of the ultrasound imaging markers 10 can be placed around the perimeter of the suspected tumor. Once the biopsy has been analyzed and found to be cancerous, the effectiveness of the chemotherapy and/or radiation therapy can be assessed by checking the positions of the plurality of ultrasound imaging markers 10 using ultrasound or radiography to see if the tumor is growing or shrinking. If the surgeon decides to remove the tumor surgically, the perimeter of the tumor can be readily ascertained with reference to the plurality of ultrasound imaging markers 10. Finally, one the tumor has been removed, another ultrasound imaging marker 10 can be left to mark the place from where the tumor was removed. In the future, if further surgery is required, or any follow-up biopsies are required, the ultrasound imaging marker 10 can be used to readily direct the surgeon back to the location 11 desired.

While the invention has been described with reference to the preferred embodiment, it is to be clearly understood by those skilled in the art that the invention is not limited thereto. Rather, the scope of the invention is to be interpreted only in conjunction with the appended claims.

What is claimed is:

1. An ultrasound imaging marker comprising:
   a marker body constructed of an ultrasound resonant material, the marker body having an interior surface and an exterior surface, the interior surface defining a resonant pocket; and
   a metallic resonant layer covering at least a portion of the marker body.
2. The ultrasound imaging marker of claim 1 wherein the resonant pocket includes a plurality of resonant bores.
3. The ultrasound imaging marker of claim 2 wherein the plurality of resonant bores are evenly spaced.
4. The ultrasound imaging marker of claim 3 wherein at least some of the plurality of resonant bores are between 50–150 microns deep.
5. The ultrasound imaging marker of claim 1 wherein the marker body includes a marker base and a cap, the cap being shaped to engage the marker base to define the resonant pocket.
6. The ultrasound imaging marker of claim 5 wherein the metallic resonant layer is deposited upon an inner cap surface of the cap.
7. The ultrasound imaging marker of claim 5 wherein the metallic resonant layer is deposited upon the interior surface of the marker base.
8. The ultrasound imaging marker of claim 1 wherein the metallic resonant layer is formed of alumina.
9. The ultrasound imaging marker of claim 1 wherein the metallic resonant layer is formed of gold.
10. The ultrasound imaging marker of claim 1 wherein the marker body is sealed with a biocompatible coating.
11. The ultrasound imaging marker of claim 1 wherein the marker body is constructed of biodegradable and bioresorbable plastic.
12. The ultrasound imaging marker of claim 1 wherein the marker body is constructed of silicon.
13. The ultrasound imaging marker of claim 1 further comprising a means for preventing migration of the ultrasound imaging marker within a mammalian body.
14. An ultrasound imaging marker comprising:
    a marker base having an interior surface, an angled surface, a perimeter lip, and an exterior surface,
    the interior surface being generally planar, the angled surface bounding the interior surface and connecting the interior surface with the perimeter lip, the perimeter lip defining an opening to an resonant pocket that is bounded by the interior surface and the angled surface, the perimeter lip further having a lip surface; and
    a cap having an inner cap surface and an exterior cap surface, the inner cap surface being shaped to tightly engage the lip surface of the marker base to close the opening of the resonant pocket,
    the marker base and the cap being constructed of an ultrasound resonant material.
15. The ultrasound imaging marker of claim 14 further comprising a metallic resonant layer coating the interior surface.
16. The ultrasound imaging marker of claim 14 further comprising a means for preventing migration of the ultrasound imaging marker within a mammalian body.
17. The ultrasound imaging marker of claim 16 wherein the means for preventing migration of the ultrasound imaging marker includes a pair of end caps adapted to be attached to opposing ends of the marker base.
18. The ultrasound imaging marker of claim 14 wherein the angle between the interior surface and the angled surface is between 120–140 degrees.
19. A surgical marking system comprising:
    at least one ultrasound imaging marker having a marker body constructed of an ultrasound resonant material, the marker body having an interior surface and an exterior surface, the interior surface defining a resonant pocket; and
    an insertion device having a cannula with an insertion tip having an interior cannula chamber shaped to receive the at least one ultrasound imaging marker and dispense the at least one ultrasound imaging marker through a cannula opening of the insertion tip, the insertion device further having a means for ejecting one of the at least one ultrasound imaging marker upon actuation of a trigger.
20. The ultrasound imaging marker of claim 19 wherein the at least one ultrasound imaging marker further includes a metallic resonant layer covering at least a portion of the interior surface.
21. An ultrasound imaging marker comprising:
    a marker body constructed of an ultrasound resonant material, the marker body having an interior surface and an exterior surface, the interior surface being etched to provide a roughened surface; and
    a means for preventing migration of the marker body within a mammalian body.
22. The ultrasound imaging marker of claim 21 wherein the roughened surface includes a plurality of resonant bores.
23. The ultrasound imaging marker of claim 22 wherein the plurality of resonant bores are evenly spaced.
24. The ultrasound imaging marker of claim 23 wherein at least some of the plurality of resonant bores are between 50–150 microns deep.
25. The ultrasound imaging marker of claim 21 wherein the marker body is at least partially coated with a metallic resonant layer.
26. The ultrasound imaging marker of claim 21 wherein the ultrasound resonant material is silicon.

* * * * *